United States Patent [19]

Rosenthal

[11] Patent Number: 5,068,536

[45] Date of Patent: Nov. 26, 1991

[54] METHOD FOR PROVIDING CUSTOM CALIBRATION FOR NEAR INFRARED INSTRUMENTS FOR MEASUREMENT OF BLOOD GLUCOSE

[75] Inventor: Robert D. Rosenthal, Gaithersburg, Md.

[73] Assignee: Futrex, Inc., Gaithersburg, Md.

[21] Appl. No.: 682,249

[22] Filed: Apr. 9, 1991

Related U.S. Application Data

[63] Continuation-in-part of Ser. No. 565,302, Aug. 10, 1990, which is a continuation-in-part of Ser. No. 544,580, Jun. 27, 1990, which is a continuation-in-part of Ser. No. 298,904, Jan. 19, 1989, Pat. No. 5,028,787.

[51] Int. Cl.$^5$ ............................................. G01N 21/59
[52] U.S. Cl. ..................................... 250/341; 128/633
[58] Field of Search ...................... 250/339, 341, 343; 356/39; 128/633

[56] References Cited

U.S. PATENT DOCUMENTS

| | | | |
|---|---|---|---|
| 4,882,492 | 11/1989 | Koashi et al. | 250/341 |
| 4,883,953 | 11/1989 | Schlager | 250/341 |
| 5,009,230 | 4/1991 | Hutchinson | 128/633 |

Primary Examiner—Edward P. Westin
Assistant Examiner—Richard Hanig
Attorney, Agent, or Firm—Rothwell, Figg, Ernst & Kurz

[57] ABSTRACT

A method is disclosed for easily and reliably custom calibrating near-infrared quantitative analysis instruments including obtaining a plurality of blood samples and blood glucose level measurements thereof at a predetermined time interval. These values are entered into the analysis instrument. Near-infrared optical measurements of the individual are simultaneously taken using the analysis instrument at another predetermined time interval. Calibration regression analysis is performed on the data to custom calibrate the analysis instrument which involves linearly interpolating the blood sample glucose measurements with the near-infrared optical recordings.

11 Claims, 4 Drawing Sheets

METHOD FOR PROVIDING CUSTOM CALIBRATION FOR NEAR INFRARED INSTRUMENTS FOR MEASUREMENT OF BLOOD GLUCOSE

BACKGROUND OF THE INVENTION

Cross-Reference to Related Application

This application is a continuation-in-part of copending application Ser. No. 07/565,302, filed Aug. 10, 1990, which is a continuation-in-part of copending application Ser. No. 07/544,580, filed June 27, 1990, which is a continuation-in-part of copending application Ser. No. 07/298,904, filed Jan. 19, 1989, now U.S. Pat No. 5,028,787.

FIELD OF THE INVENTION

The invention relates to instruments and methods for the non-invasive quantitative measurement of blood glucose. More specifally, this invention relates to a method for providing custom calibration for near infrared instruments for measurement of blood glucose.

DESCRIPTION OF BACKGROUND ART

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation is available for the specific purpose of determining blood glucose levels in people with diabetes. This technology uses a small blood sample from a finger poke which is placed on a chemically treated carrier and is inserted into a portable battery operated instrument. The instrument analyzes the blood sample and provides a blood glucose level reading in a short period of time.

A different class of blood glucose analytical instruments is the near-infrared quantitative analysis instrument which non-invasively measures blood glucose, such as the type described in copending application Ser. No. 07/565,302. The noninvasive blood glucose measurement instrument analyzes near-infrared energy following interactance with venous or arterial blood, or transmission through a blood containing body part. These instruments give accurate blood glucose level readings and readily lend themselves to at-home testing by diabetics.

A limitation of the near-infrared blood glucose measurement instruments is that each may be required to be custom calibrated for each individual user. The need for individual custom calibration results from the different combination of water level, fat level and protein level in various individuals which causes variations in energy absorption. Since the amount of glucose in the body is less than one thousandth of these other constituents, variations of these constituents which exist between people may make a universal calibration unlikely.

The current approach for custom calibrating near-infrared blood glucose measurement instruments is to use an in vitro technique that requires removing blood from the subject and having an automatic instrument measure the glucose level of that blood. Such in vitro measurements are typically made with either the commercially available Biostator or the experimental Kowarski Continuous Monitor. Each of the above instruments requires a catheter to be inserted into the subject and blood withdrawn over a one to two hour period. Although such an approach is feasible, it places a significant new burden on the doctor and the medical facility to have enough time, room and equipment to be able to calibrate instruments in this fashion.

Thus, there is a great need for a technique which allows an individual user to easily and reliably custom calibrate the near-infrared instrument.

SUMMARY OF THE INVENTION

In accordance with the present invention, a low-cost method and means for providing custom calibration for near-infrared instruments for measurement of blood glucose comprises obtaining a plurality of blood samples from an individual at a predetermined time interval and for a predetermined period of time. Blood glucose measurements for each blood sample are obtained and are entered into the near-infrared instrument. Noninvasive near-infrared optical absorption measurements are concomitantly taken through a body part of the individual at a second predetermined time interval and are recorded in the analysis instrument. Calibration regression analysis is then performed utilizing means for linearly interpolating the blood sample glucose measurements with the near-infrared optical measurements to custom calibrate the near-infrared instrument for the individual.

Another aspect of the present invention relates to a method of compensating for calibration errors resulting from changes in an individual's skin temperature. This technique involves producing a change in the individual's skin temperature while obtaining the noninvasive near-infrared blood glucose measurements. The individual's skin temperature is thereby forced to have a meaningful temperature range during the calibration process.

DETAILED DESCRIPTION OF THE PREFERRED EMBODIMENTS

The present invention is directed toward a method for custom calibrating a noninvasive near-infrared blood glucose measurement instrument for an individual user. An example of such a near-infrared blood glucose instrument is illustrated in copending application Ser. No. 07/565,302, incorporated herein by reference.

In conventional near-infrared analysis, the calibration procedure requires a significant number of "samples"

(i.e. a set of optical measurements) with known laboratory analysis of the parameter of interest (e.g. protein in wheat). The need for individual laboratory analyzed samples in conventional analysis results from the fact that each sample, and accordingly the parameter measurement, is totally independent of the previous sample. For example, when calibrating an instrument to measure protein in wheat, each wheat sample requires separate laboratory analysis.

However, in custom calibration for blood glucose, that a priori assumption is not true. It is known that if a diabetic eats food, a diabetic's blood glucose level will increase over the next fifteen minutes to a half an hour. This known characteristic of the direction of change in an individual's blood glucose level is an important factor for simplified custom calibration.

Figure 1:
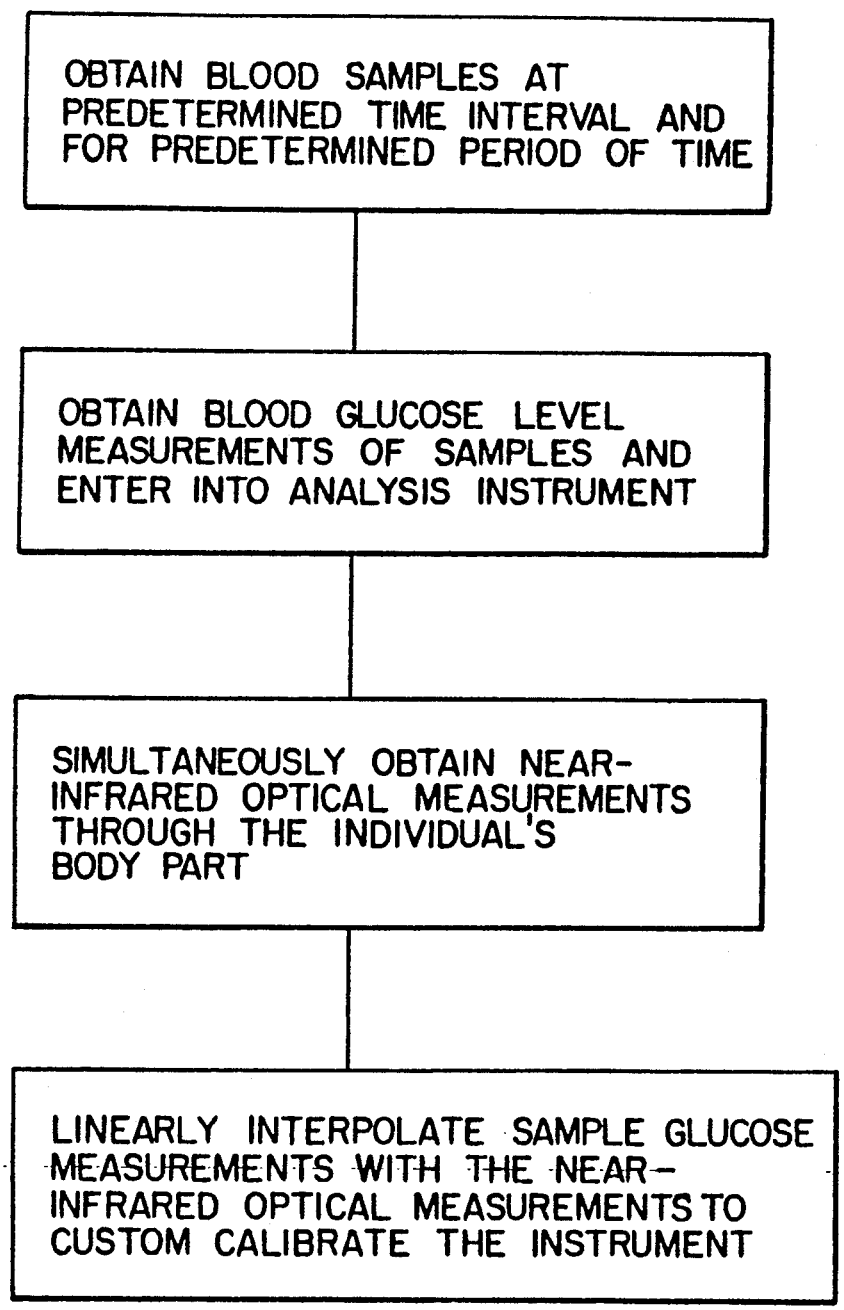
FIG. 1 is a flow diagram illustrating the method for custom calibrating a near-infrared analysis instrument for the measurement of blood glucose levels according to the present invention.

According to the present invention, FIG. 1 illustrates an easy and reliable method for custom calibration wherein a plurality of blood samples are obtained from an individual at predetermined time intervals, which do not need to be of equal duration, and for a predetermined period of time. Blood glucose levels are then obtained for each blood sample by any suitable reference method such as a Glucose Meter 2300G, manufactured by Yellow Springs Instrument Co. This information will serve as the laboratory data. The blood samples and blood glucose level measurements can be obtained using any other suitable means, such as a commercially available Biostator.

In a preferred embodiment, the blood glucose level measurements are obtained from a widely available Self-Monitoring Glucose Meter ("SMGM"). The technique employed in SMGM's involves using a lancet to draw blood from a finger tip. A drop of blood is then placed on a chemically loaded plastic strip which is inserted into the instrument. The instrument measures and then digitally displays the blood glucose levels.

The predetermined time period in which the blood samples are taken is typically approximately once every 10-20 minutes and for approximately one half hour to an hour and a half. The blood glucose level data is then entered into any suitable computation instrument, such as a computer, which can perform multiple regression analysis. In a preferred embodiment, the blood glucose level data is entered into the near-infrared analysis instrument.

Also in a preferred embodiment, the predetermined time interval is selected so as to obtain actual blood glucose measurements at different levels while the individual's blood is being "spiked" (i.e. caloric ingestion). For example, a first blood glucose reading is taken after an overnight fast. Following this reading, the individual will either take and ingest a dextrose solution or eat a meal which will elevate the individual's blood glucose level. An additional finger poke measurement is then made after approximately fifteen minutes. This is repeated approximately every fifteen minutes for one hour. A total of four finger poke measurements are taken, in the preferred embodiment. The sample blood glucose level measurements could also be taken at predetermined time intervals which are not of equal duration, for example, after ten minutes, twenty-five minutes, forty-five minutes and after one hour and ten minutes. The predetermined time interval can be any time interval which will enable the individual's blood glucose level to be measured during at least a period where the individual's blood glucose level changes.

During the time period in which the blood samples are taken, near-infrared optical measurements are made and recorded using the noninvasive blood glucose instrument. These optical measurements should be made approximately once per minute. A total of approximately 60 sets of optical information will be recorded in the preferred embodiment.

The method of the present invention is utilized to calibrate a near-infrared analysis instrument not only for blood glucose levels, but for any known characteristic of the blood. For example, a priori knowledge of insulin level characteristics in the body is known and the method of the present invention could be used to calibrate a near-infrared instrument for measurement of insulin levels.

The calibration regression analysis performed on the optical measurements will be described hereinafter. The calibration regression analysis of the present invention utilizes means for linearly interpolating the blood glucose level measurements made from the individual blood samples with the near-infrared optical measurements. Specifically, linear interpolation is used to assign laboratory values to the near-infrared optical measurements, between adjacent pair of the four finger poke glucose level measurements, which are taken at approximately fifteen minutes apart in the preferred embodiment. The linear interpolation is performed to provide glucose values for the specific times that the optical measurements are made, thus becoming the independent variable of the regression analysis. Thus, in the preferred embodiment, a set of four actual finger poke measurements will provide information for approximately sixty sets of the near-infrared optical measurements. The regression analysis is performed by a signal processor in any suitable method, such as the manner set forth copending patent application Ser. No. 07/565,302.

Since linear interpolation involves mathematically assigning expected values based on known values using an interpolation algorithm, the potential for error exists. In near-infrared analysis, it is known that the laboratory value assigned at any particular time by the interpolation process will potentially be in error from the actual blood glucose value at that moment. These errors typically result from the inaccuracy of the SMGM readings and from errors due to using interpolated values between the times of SMGM readings.

Although potential for error in the interpolated values exists, considerable experimentation in near-infrared technology has shown that such errors do not significantly affect calibration accuracy. The reason that accuracy is not significantly sacrificed is that the number of calibration samples, i.e. near-infrared optical measurements, is much larger than the number of regression terms in the regression algorithm. For example, the regression analysis performed in the present invention, illustrated in copending application Ser. No. 07/565,302, uses approximately three regression terms. Typically, acceptable accuracy occurs in near-infrared calibration where approximately ten samples are used for each regression term. In a preferred embodiment, approximately sixty samples are used and the total number of regression terms is approximately three or four. Thus, approximately fifteen samples per regression term are used. Moreover, this procedure can be repeated over several days which will enhance the statistical significance.

Figure 2:
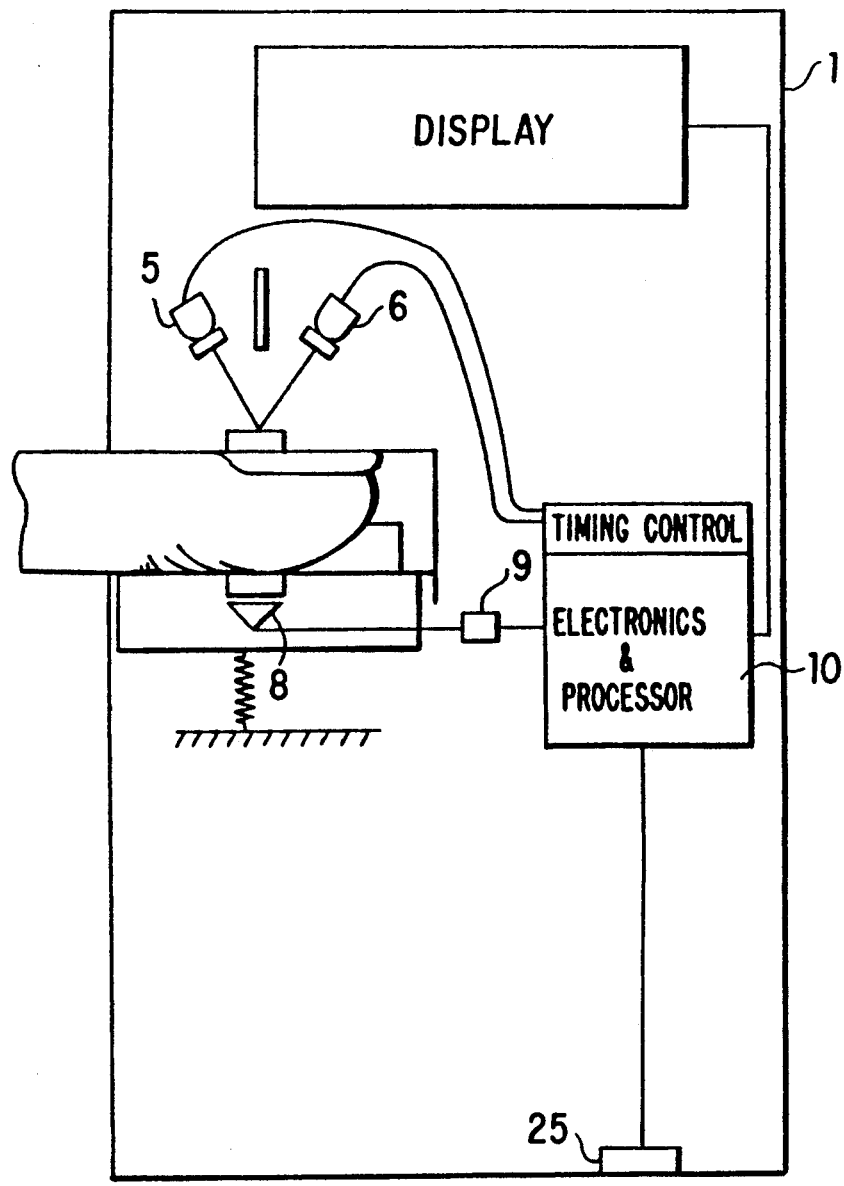
FIG. 2 is a schematic illustration of a noninvasive near-infrared glucose meter which is custom calibrated according to the method of the present invention.

A near-infrared noninvasive blood glucose measurement instrument which can be custom calibrated employing the method of the present invention is illustrated schematically in FIG. 2. Noninvasive glucose meter 1 is designed to measure blood glucose levels through the distal portion of the test subject's finger. The analytical instrument contains at least one near-infrared energy source for introducing near infrared energy into the test subject's finger. Near-infrared point sources 5 and 6 are shown for illustrative purposes in FIG. 2. The analytical instrument also utilizes detector 8 for detecting near-infrared energy emerging from the test subject's body part. Detector 8 is electrically connected to signal processing means 10 which, according to its programming, processes the signal produced by the detector 8 into a signal indicative of the quantity of glucose present in the blood of the test subject. Amplifier 9 amplifies the signal produced by the detector 8 before it is received into the processing means 10. Input/output connector 25 is electrically connected to the processing means 10 and allows the analytical instrument 1 to be connected to a "host instrument" such as a computer. Input/output connector 25 enables the individual sample blood glucose level measurements to be entered into the analysis instrument. In a preferred embodiment, the calibration regression analysis is performed using signal processor contained within the analytical instrument itself.

Also in a preferred embodiment, the need to provide a data link to a host computer is eliminated by enabling the individual sample blood glucose level measurements to be entered into the analytical instrument through a keyboard on the instrument itself (not shown).

The method for custom calibrating a non-invasive blood glucose measurement instrument according to the present invention can also be used to calibrate analytical instruments which utilize near-infrared reflectance or interactance, such as the instruments disclosed in copending application Ser. No. 07/298,904.

This novel method overcomes the inconveniences of the prior art methods by providing easy and reliable custom calibration of noninvasive blood glucose measurement instruments which can readily be done on an at-home basis.

Additional embodiments of near-infrared noninvasive blood glucose measurement instruments which can be custom calibrated according to the method of the present invention will be described with reference to FIGS. 3 and 4.

Figure 3:
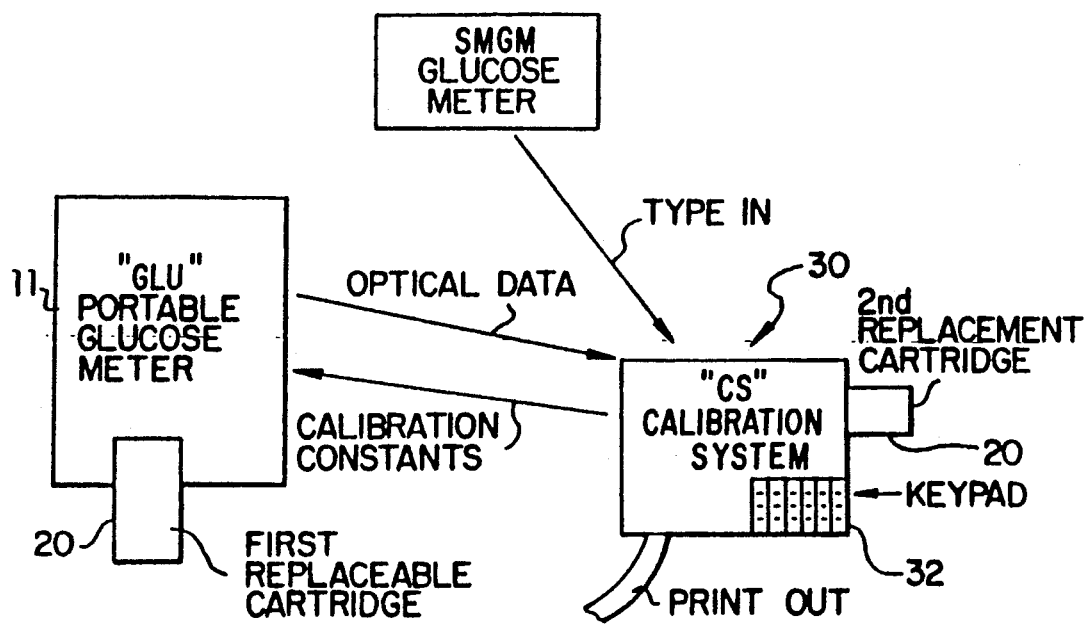
FIG. 3 is a schematic illustration of custom calibration system in accordance with the present invention.
Figure 4:
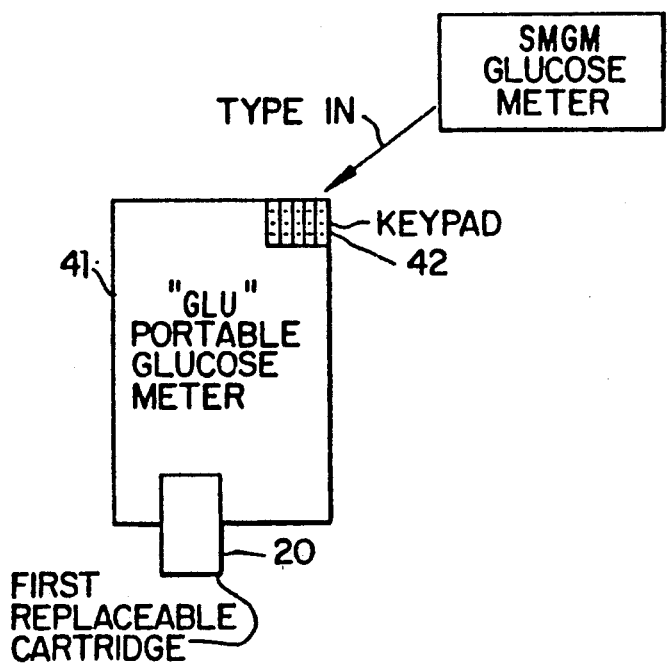
FIG. 4 is a schematic illustration of a different embodiment of a custom calibration system according to the present invention.

The near-infrared analytical instruments 11 and 41, illustrated in FIGS. 3 and 4 respectively, operate substantially identically as disclosed in copending application Ser. No. 07/565,302. The custom calibration procedure will be described in two alternate methods. First, as illustrated in FIG. 3, a calibration system 30 is connected to the analytical instrument 11 and collects both optical data as measurements are taken and the time of each measurement. The calibration system 30 also allows the glucose values from the finger poke measurements to be hand entered via keypad 32 on the calibration system 30 at approximately 15 minute intervals for up to 1.5 hours. When sufficient data has been received, such as after the above-described predetermined time intervals, the calibration system performs a multiple regression analysis, calculating the calibration constants for the linear regression algorithms. The calculated calibration constants are then transferred to the replaceable cartridges 20 plugged into the calibration system 30, or into a replaceable cartridge installed in the analytical instrument 11, and another inserted into the calibration system 30. In this approach, the calibration system 30 could be in a doctor's office and could also provide a printout device for the replaceable cartridges.

An alternate approach, illustrated in FIG. 4, does not require a calibration system as discussed above. In this approach, the replaceable cartridge contains EPROMs programmed to perform multiple regression analysis. The analytical instrument 41 has a key pad 42 having, typically, 11 keys (e.g. "0" through "9" plus an ENTER key) to allow the finger poke readings to be entered. In another embodiment, the finger poke readings are entered from an external keyboard or a replaceable cartridge. After the regression analysis is performed, the analytical instrument stores the calibration constants in the replaceable cartridge. At the same time, the analytical instrument erases the regression program allowing the EPROM to be used to store time/data and glucose values for a predetermined period of time, e.g., three months.

In another aspect of the invention, a method is disclosed for providing custom calibration which is valid over a range of skin temperatures. It is well established that temperature affects the energy absorption in near-infrared water band. See copending application Ser. No. 07/544,580, incorporated herein by reference. Further, since the human body does not maintain constant temperatures at the extremities, i.e. fingers, calibration accuracy can be improved by including the affects of temperature variation.

The affect of temperature variations in blood glucose calibration has a direct applicable analogy in near-infrared (NIR) agricultural instruments. For example, if calibration for measurement of protein in wheat is performed with all wheat samples near room temperature, large errors would occur if that calibration is then used to predict the protein in wheat samples at significantly different temperatures.

This potential error is largely avoided by deliberately changing the temperature of samples during wheat calibrations. For example, some wheat samples are stored in a refrigerator and then immediately measured on an NIR instrument. Other wheat samples are stored in freezers and then immediately measured on the NIR instrument. This approach has proven to be very successful for agricultural products, such as wheat, and has proven to provide accurate measurements at extreme temperatures.

An analogous approach provides accurate blood glucose calibration. Specifically, an individual's finger temperature is forced to have a range during the calibration process. Optical recordings are taken during the calibration at a range of skin temperatures.

Finger temperature variations can be induced using any conventional approach. For example, according to one technique of the present invention a small vessel is filled with water at room temperature. The individual to be tested then inserts the hand into a plastic bag leaving the top edge of the bag open. The bagged hand is then inserted into the water avoiding water contact with the skin. The hand is left in the water for at least one minute. Good heat transfer will result as the water pressure will force the air out of the plastic bag thereby snugly pressing the plastic against the hand. The hand is then removed and the near-infrared measurement is performed. The above-described steps are then repeated using water having a different temperature, i.e. approximately 100° to 120° F. Although any number of different temperature measurements could be used, the above approach allows the calibration to be performed with three different temperatures, including a measurement with no water immersion.

A test was performed to illustrate the effect of temperature variation on optical absorption wherein separate near-infrared measurements were taken for three finger temperature variations: (1) Hand in plastic bag immersed for 60 seconds in cool tap water (55° F.); (2) Normal skin temperature (no water immersion); and (3) Hand in plastic bag immersed for 60 seconds in warm water (103° F.).

TABLE 1

| | Measured Finger Temperature | Peak Optical Absorption | Rate of Shift |
| --- | --- | --- | --- |
| Cool tap Water (55° F.) | 30.8° C. | 972.3 nm | $\frac{972.3 - 971.8}{30.8 - 34.3} =$ $-0.14$ nm/°C. |
| No Water Immersion | 32.9° C. | 972.0 nm | |
| Warm Tap Water (103° F.) | 34.3° C. | 971.8 nm | |

The test results set out in Table 1 above illustrate that the peak optical absorption shifts with finger temperature at a rate of approximately $-0.14$ nm/°C.

Figure 5:
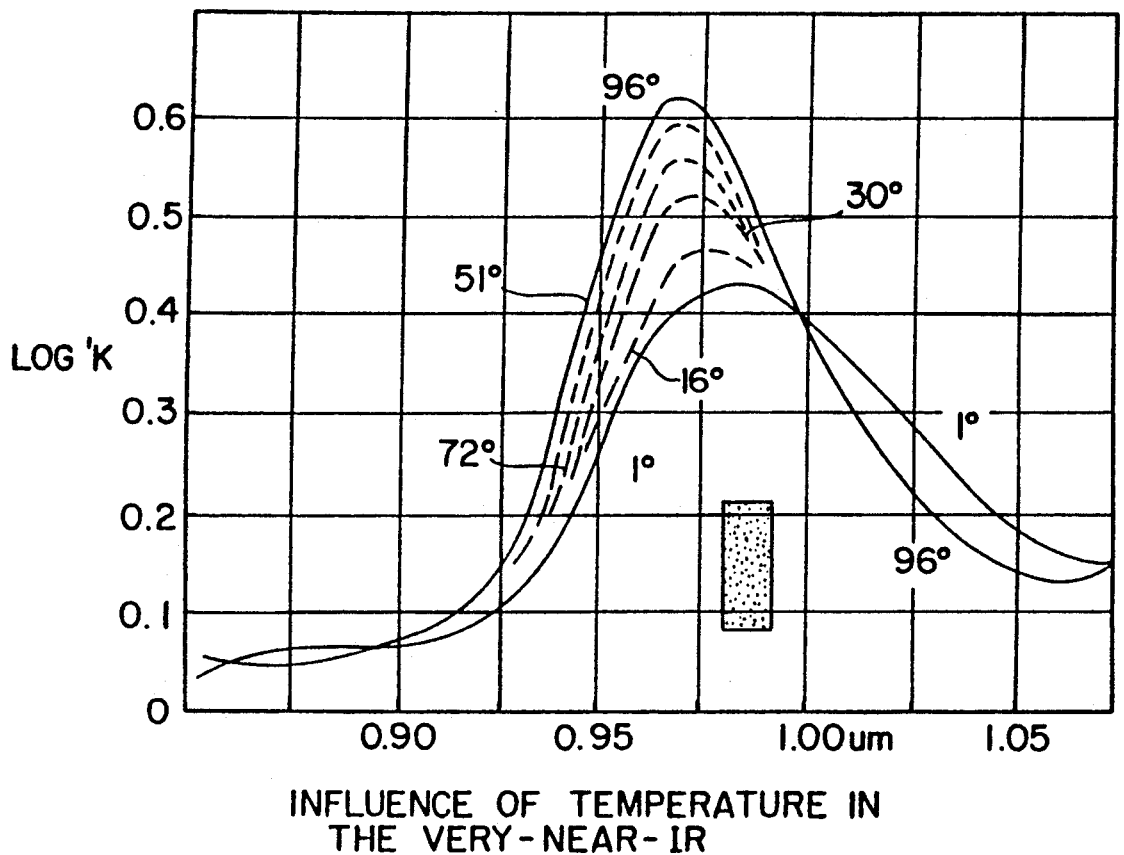
FIG. 5 is a graph showing near-infrared energy absorption by water as a function of temperature.

The rate of wavelength shift resulting from finger temperature variation is compared with the rate of wavelength shift caused by temperature variations in water. The magnitude of the wavelength shift can be calculated from the data in FIG. 5.

Peak wavelength at 11° C. = 980 nm
Peak wavelength at 96° C. = 970 nm
Rate Of Shift = 980 − 970/1 − 96 = −0.11/° C.

The test results indicate that the measured rate of shift is essentially identical for the finger measurement as it is for pure water. This illustrates that imposing a temperature variation in the glucose calibration, the calibration will have greater validity over all finger temperatures.

Although the invention has been described in connection with certain preferred embodiments, it is not limited to them. Modifications within the scope of the following claims will be apparent to those skilled in the art. For example, accurate measurements can be obtained from body parts other than the wrist and the finger. The algorithm used to calculate blood constituent concentration(s) can be altered in accordance with known near-infrared analytical techniques.

I claim:

1. A method for calibrating a near-infrared analysis instrument for the measurement of blood glucose, said method comprising:
   (a) obtaining a plurality of blood samples from an individual each at a first predetermined time interval during a predetermined period of time and obtaining a blood glucose level measurement for each said blood sample;
   (b) obtaining near-infrared optical absorption measurements through a body part of said individual at a second predetermined time interval and during said predetermined period of time, and recording said measurements; and
   (c) performing calibration regression analysis utilizing means for linearly interpolating said blood sample glucose level measurements with said near-infrared optical absorption measurements to calibrate said near-infrared analysis instrument for said individual.

2. The method as set forth in claim 1 wherein said first predetermined time interval is between approximately 10 and approximately 20 minutes.

3. The method as set forth in claim 1 wherein said second predetermined time interval is between approximately one and approximately three minutes.

4. The method as set forth in claim 1 wherein said predetermined period of time is between approximately 45 and approximately 90 minutes.

5. The method as set forth in claim 4 wherein said predetermined period of time is approximately 60 minutes.

6. The method as set forth in claim 2 wherein said first predetermined time interval is approximately 15 minutes.

7. The method as set forth in claim 1 wherein said first predetermined time interval comprises time periods at least one of which has an unequal duration relative to at least one other of said time periods.

8. The method as set forth in claim 1 wherein approximately 40 to approximately 90 optical absorption measurements are made.

9. The method as set forth in claim 8 where a regression analysis algorithm used in said linear interpolation utilizes approximately three or four regression terms.

10. The method as set forth in claim 1 further comprising the following steps:
    (a) placing said body part in a plurality of environments, each of said environments having a temperature different from each other of said environments, and producing a temperature change in said body part from a normal temperature of said body part; and
    (b) obtaining at least one of said near-infrared optical absorption measurements through said body part after said temperature change has been produced in said body part.

11. A method for calibrating a near-infrared analysis instrument for the measurement of an unknown value of an known characteristic of blood, said method comprising:
    (a) obtaining a plurality of blood samples from an individual each at a first predetermined time interval during a predetermined period of time and obtaining a value of said known characteristic for each blood sample;
    (b) obtaining near-infrared optical absorption measurements through a body part of said individual at a second predetermined time interval and during said predetermined period of time, and recording said measurements; and
    (c) performing calibration regression analysis utilizing means for linearly interpolating each said value of said known characteristic for each said blood sample with said near-infrared optical absorption measurements to calibrate said near-infrared analysis instrument for said individual.

* * * * *